(12) United States Patent
Disteldorf et al.

(10) Patent No.: US 7,385,075 B2
(45) Date of Patent: Jun. 10, 2008

(54) METHOD FOR PRODUCING ESTERS OF MULTIBASIC ACIDS

(75) Inventors: Walter Disteldorf, Wachenheim (DE); Günther Golfier, Frankenthal (DE); Bernd Morsbach, Ludwigshafen (DE); Kurt Schwirten, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 132 days.

(21) Appl. No.: 10/416,465

(22) PCT Filed: Nov. 13, 2001

(86) PCT No.: PCT/EP01/13131

§ 371 (c)(1), (2), (4) Date: May 12, 2003

(87) PCT Pub. No.: WO02/38531

PCT Pub. Date: May 16, 2002

(65) Prior Publication Data

US 2004/0030175 A1 Feb. 12, 2004

(30) Foreign Application Priority Data

Nov. 13, 2000 (DE) ................ 100 56 179

(51) Int. Cl.
*C07C 69/76* (2006.01)
(52) U.S. Cl. .......................... 560/89; 560/91
(58) Field of Classification Search ............ 560/44, 560/54, 76, 103, 151, 180, 190
See application file for complete search history.

(56) References Cited

U.S. PATENT DOCUMENTS

| 2,587,904 | A | * | 3/1952 | Cornelius ............. 560/198 |
| 4,119,593 | A | | 10/1978 | Smith et al. ............ 260/18 EP |
| 4,216,337 | A | * | 8/1980 | Baba et al. ............ 560/78 |
| 5,324,853 | A | | 6/1994 | Jones et al. |
| 5,696,303 | A | | 12/1997 | Darsow et al. |

FOREIGN PATENT DOCUMENTS

| GB | 1122538 | 8/1968 |
| GB | 1565663 | 4/1980 |
| GB | 1603620 | 11/1981 |
| GB | 1061173 | 3/1997 |
| JP | 51-029460 | 3/1976 |
| JP | 53-142434 | 12/1978 |
| JP | 56-040645 | 4/1981 |
| JP | 10-338742 | 12/1998 |

OTHER PUBLICATIONS

Perry, Chemical Engineer's Handbook, Fourth edition (1963).*
Ullmann's Enc. Ind. Chem., XP-002193336 Zeitschrift fur Physikalische Chemie Neue Folge, Bd 20 s. 219-232 (1959).
Uchida et al., English language translation of document AC.
Harada et al., English language translation of document AD.
Kitago et al., English language translation of document AF.
Sumisu et al., "*Polyepoxide high solid coating*"—Partial translation of document AE.
Flick, "*Industrial Solvents Handbook*"—Noyes Data Corporation, Park Ridge, NY, USA 1991, pp. 417,469,541, and 576.

* cited by examiner

*Primary Examiner*—Karl Puttlitz
(74) *Attorney, Agent, or Firm*—Novak Druce + Quigg LLP

(57) ABSTRACT

A process is described for preparing esters of an acid component selected from among polybasic $C_4$-$C_{10}$ carboxylic acids and an alcohol component selected from among $C_3$-$C_{12}$ alkanols or from among $C_3$-$C_{12}$ alkanediols, the alkyl chain of which may have interruption by from 1 to 3 oxygen atoms, by a) heating at boiling point, in a reaction zone and in the presence of an esterification catalyst, a mixture essentially consisting of the acid component or of an anhydride thereof and of the alcohol component, b) using rectification to separate the vapor comprising alcohol and water into an alcohol-rich fraction and a water-rich fraction, and c) returning the alcohol-rich fraction into the reaction zone and conducting the water-rich fraction out of the process. The process is simple to carry out and permits rapid achievement of essentially quantitative conversion.

6 Claims, No Drawings

METHOD FOR PRODUCING ESTERS OF MULTIBASIC ACIDS

This application is a National Stage application of International Application No. PCT/EP01/13131, filed 13 Nov. 2001, which application claims benefit of German Application No. DE 100 561 79.9, filed 13 Nov. 2000.

The present invention relates to a process for preparing esters of an acid component selected from among polybasic $C_4$-$C_{10}$ carboxylic acids and an alcohol component selected from among $C_3$-$C_{12}$ alkanols or from among $C_3$-$C_{12}$ alkanediols, the alkyl chain of which may have interruption by from 1 to 3 oxygen atoms.

Esters of the type mentioned are widely used as plasticizers in plastics, such as cellulose acetates, polyurethanes, PVC, polyacrylates, etc. They may be prepared by reacting the acid component or an anhydride thereof with the alcohol component in the presence of an esterification catalyst. The reaction is an equilibrium reaction. The equilibrium may be shifted to the product side, i.e. the ester side, by continuous removal of the water produced as by-product from the reaction. If the alcohol used has a region in which it is not miscible with water, it is possible to distill off continuously from the reaction mixture a mixture of the water of the reaction and alcohol, and, after phase separation, to return the organic phase to the esterification, while the aqueous phase is removed from the system. Since water is always soluble to some extent in the alcohol, water is also returned with the organic phase, and the shift of the equilibrium to give quantitative conversion sometimes therefore proceeds very slowly.

If ethylene glycol monobutyl ether is used, for example, the region of immiscibility with water exists only at from 43° C. to 133° C. (cf. G. Schneider and G. Wilke, Zeitschr. f. Phys. Chemie, NF, 20, 219 (1959)), and in this case, therefore, the phase separator has to be held disadvantageously at a temperature between the two limiting points of mixing. In addition, the alcohol phase as it returns still comprises 39.7% by weight of water.

It is an object of the present invention to provide a process for preparing the esters mentioned at the outset which is simple to carry out and within a short time leads to essentially quantitative conversion.

We have found that this object is achieved by
a) heating at boiling point, in a reaction zone and in the presence of an esterification catalyst, a mixture essentially consisting of the acid component or of an anhydride thereof and of the alcohol component,
b) using rectification to separate the vapor comprising alcohol and water into an alcohol-rich fraction and a water-rich fraction,
c) returning the alcohol-rich fraction into the reaction zone and conducting the water-rich fraction out of the process.

The acid component is a polybasic, in particular dibasic, carboxylic acid having from 4 to 10 carbon atoms. It may be aromatic or aliphatic. Examples of those which may be used are succinic acid, glutaric acid, adipic acid, pimelic acid, suberic acid, azelaic acid, sebacic acid, hexahydro phthalic acid, hexahydro isophthalic acid or hexahydro terepthalic acid, and also phthalic acid, isophthalic acid and terephthalic acid. Of these, adipic acid and phthalic acid are particularly preferred. The acid component may be used as such or in the form of an anhydride, e.g. of an intra- or intermolecular anhydride. For example, phthalic acid is usually used in the form of the industrially available compound phthalic anhydride.

The alcohol component is a branched or straight-chain alkanol or alkanediol having from 3 to 12 carbon atoms, preferably from 3 to 8 carbon atoms, and the alkyl chain of the alkanol or alkanediol may have interruption by from 1 to 3, in particular 1 or 2, oxygen atoms in ether bonding. If more than one oxygen atom is present, there are preferably at least two carbon atoms separating these from one another. It is also possible to use mixtures of different alkanols or alkanediols or of alkanols and alkanediols. Examples of alkanols which may be used are n-propanol, i-propanol, n-butanol, sec-butanol, tert-butanol, pentanol, hexanol, heptanol, octanol, isooctanol, 2-ethylhexanol and also ethylene glycol monomethyl ether, ethylene glycol monoethyl ether and ethylene glycol monobutyl ether. Examples of alkanediols which may be used are 1,2-propanediol, 1,3-propanediol, 1,3-butanediol, 1,4-butanediol, neopentyl glycol and 1,6-hexanediol. Of these, particular preference is given to n-butanol, 2-ethylhexanol, ethylene glycol monoethyl ether and ethylene glycol monobutyl ether.

The esters of the alkanediols obtained according to the present invention are generally polymeric compounds with weight-average molecular weights of from about 1800 to 13000. For producing these polymeric esters, the alkanediols are generally used in a mixture with alkanols, wherein the latter are used as chain-terminating agents.

It is preferable for the alcohol component to be used in a molar excess over the acid component, e.g. in an excess of up to 500%, preferably up to 200%, in particular up to 100%, particularly preferably from 20 to 60%, based on the stoichiometrically necessary amount. The process of the invention is carried out in the absence of any external entrainer.

Esterification catalysts which may be used are conventional catalysts usually used for esterification reactions. These include mineral acids, such as sulfuric acid, phosphoric acid; organic sulfonic acids, such as methanesulfonic acid, p-toluenesulfonic acid; Lewis acids, in particular titanium, tin(IV) or zirconium compounds, such as tetraalkoxytitanium compounds, e.g. tetrabutoxytitanium, and tin(IV) oxide.

An effective amount of the esterification catalyst is used and is usually in the range from 0.05 to 5% by weight, preferably from 0.1 to 1% by weight, based on the entirety of acid component (or anhydride) and alcohol component.

The mixture of acid component or the anhydride thereof, alcohol component and esterification catalyst is heated at boiling point. The pressure and temperature conditions required for this purpose are highly dependent on the alcohol component used. A general guide which may be given is from 140 to 220° C. and a pressure of from 0.3 to 2 bar. It is often advantageous to raise the temperature during the course of the reaction and/or to lower the pressure.

Any of the commonly used heatable reactors is suitable for carrying out the process of the invention, e.g. a stirred tank reactor.

In an advantageous method, the vapor comprising alcohol and water is returned into a column for separation by rectification, and the product being discharged from the lower end of the column, i.e. the bottom product, is returned into the reaction zone as alcohol-rich fraction, and the distillate is conducted out of the process.

The column may be a conventional column known to the skilled worker, such as a packed column or a plate column. The packed columns may be of glass, ceramic material or metal, e.g. Raschig rings, saddles, beads, spirals, other rings, and the like. An example of a suitable number of theoretical plates of the column is from 8 to 12. The lower end of the column has a connection to the vapor space of the reaction zone permitting the passage of gas. In an advantageous method, all of the rectified vapor emerging at the upper end of the column is condensed. Some or all of the condensate is taken off as distillate. The portion not taken off as distillate is returned into the column as runback. A particularly advantageous runback ratio R/D has proven to be from 1:2 to 1:10. If the condensate forms both phases, it is useful to recycle the organic phase completely and to withdraw the aqueous phase at least in part.

For the purposes of the present invention, the terms "alcohol-rich" fraction and "water-rich" fraction mean that the respective fraction has been enriched in alcohol or, respectively, enriched in water when compared with the composition of the vapor drawn off from the reaction zone. The alcohol-rich fraction preferably has an alcohol content of more than 80% by weight, particularly more than 95% by weight. It is particularly preferably essentially pure alcohol.

Once the desired conversion has been achieved, if the reaction is being operated batchwise it is generally stopped, and the excess alcohol component is distilled off. The desired ester may be isolated from the residue using conventional processes, e.g. extraction to remove the catalyst or the hydrolysis products thereof from the residue, followed by distillation. As an alternative, the process of the invention may be carried out continuously, and an advantageous method for this purpose is to use an arrangement of main reaction zone and post reaction zone, or a cascade of reaction zones. Here, the vapor from at least one of the reaction zones and preferably from the main reaction zone is separated as described, the vapor from each of the reactors being rectified on its own or combined and rectified jointly. The runback of the alcohol-rich fraction takes place into the respective reaction zone, or the fraction is divided as required among each of the reaction zones.

In an advantageous method, the water-rich fraction is worked up in order to reclaim the alcohol component present therein. It is often possible to make use of the fact that—as is the case with ethylene glycol monobutyl ether—the composition of the water-rich fraction lies within the region where the alcohol component is not miscible with water. In the case of ethylene glycol monobutyl ether the region of immiscibility occurs only at from 43° C. to 133° C. A suitable method is therefore to bring the water-rich fraction to a temperature within the range mentioned, preferably from about 60 to 90° C., in particular from 70 to 80° C., whereupon this breaks down into an organic phase with an ethylene glycol monobutyl ether content of about 60.3% by weight and an aqueous phase with about 90.4% by weight of water. The organic and/or aqueous phase may be further purified if desired by conventional processes.

The examples below will now give further illustration of the invention.

EXAMPLE 1

444 g (3 mol) of phthalic anhydride and 1063.8 g (9 mol) of ethylene glycol monobutyl ether are heated at boiling point with tetrabutoxytitanium (0.8% by weight, based on the mixture) in a 2 l three-necked flask, on top of which has been placed a packed column of length 60 cm with column head and condenser, and also a runback divider, until a significant level of runback had appeared in the runback divider. A portion of the condensate from the rectified vapor was then removed at a temperature of 99° C. After 120 minutes, a total of 75 ml of condensate had been taken off, and the acid value found on determining the acid content of the flask contents was 0.056 mg KOH/g.

COMPARATIVE EXAMPLE 1

Example 1 was repeated, but instead of the packed column a water separator had been placed on the flask, the phase separator of the water separator being a jacketed vessel. This was held at 88° C. by a thermostat. The upper phase ran continuously back into the flask. After 300 minutes the acid value of the flask content was 9.6, and after 540 minutes it was 0.12.

EXAMPLE 2

451 g (3.1 mol) of adipic acid and 792 g (7.75 mol) of n-hexan-1-ol were charged to a 2 l three-necked flask which had a stirrer and on which a 50 cm column and column head had been placed. 0.5% of methanesulfonic acid was added as catalyst, and the mixture was heated at boiling point. The condensate broke down into an organic phase and an aqueous phase. The manner of operating the column head was such that all of the organic phase was used as runback, while the aqueous phase was used as runback and also taken off at the column head. The column head temperature was from 95° C. to 100° C. After 110 minutes the acid value of the flask contents was 0.35.

COMPARATIVE EXAMPLE 2

Example 2 was repeated, but the column was replaced by a water separator. All of the organic phase was used as runback, while the aqueous phase was drawn off. After 240 minutes the acid value in the flask contents was 0.7.

We claim:

1. A process for preparing esters of an acid component from among polybasic $C_4$-$C_{10}$ carboxylic acids and an alcohol component selected from among ethylene glycol monobutyl ether, n-hexanol-1, and 2-ethylhexanol by
   a) heating at boiling point, in a reaction zone and in the presence of an esterification catalyst, a mixture consisting essentially of the acid component or of an anhydride thereof and of the alcohol component to obtain a vapor comprising alcohol and water,
   b) introducing the vapor comprising alcohol and water into a rectification column and separating the vapor into an alcohol-rich fraction and a water-rich fraction, by rectification,
   c) returning the alcohol-rich fraction being discharged from the lower end of the rectification column into the reaction zone,
      condensing all of the water-rich fraction emerging at the upper end of the column to form an organic phase and an aqueous phase,
      recycling the organic phase completely as reflux, and withdrawing from the process at least a part of the aqueous phase.

2. A process as claimed in claim 1, in which the water-rich fraction taken off out of the process is worked up in order to recover the alcohol component therein.

3. A process as claimed in claim 1, in which the acid component has been selected from among phthalic acid and adipic acid.

4. A process as claimed in claim 1, in which the esterification catalyst has been selected from among mineral acids, organic sulfonic acids and Lewis acids.

5. A process as claimed in claim 1, in which the alcohol component is ethylene glycol monobutyl ether and the anhydride component is phthalic anhydride.

6. A process as claimed in claim 1, in which the alcohol component is ethylene glycol monobutyl ether and the acid component is adipic acid.

* * * * *